US008883768B2

(12) United States Patent
King

(10) Patent No.: US 8,883,768 B2
(45) Date of Patent: Nov. 11, 2014

(54) FLUOCINOLONE IMPLANTS TO PROTECT AGAINST UNDESIRABLE BONE AND CARTILAGE DESTRUCTION

(75) Inventor: Vanja Margareta King, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 675 days.

(21) Appl. No.: 12/393,518

(22) Filed: Feb. 26, 2009

(65) Prior Publication Data

US 2009/0264391 A1 Oct. 22, 2009

Related U.S. Application Data

(60) Provisional application No. 61/046,218, filed on Apr. 18, 2008.

(51) Int. Cl.
*A61K 31/58* (2006.01)
*A61F 2/00* (2006.01)

(52) U.S. Cl.
USPC ............................................ 514/174; 424/426

(58) Field of Classification Search
USPC ......................................... 514/174; 424/78.05
See application file for complete search history.

(56) References Cited

U.S. PATENT DOCUMENTS

| | | | |
|---|---|---|---|
| 6,069,129 A | 5/2000 | Sandberg et al. | |
| 6,179,862 B1 | 1/2001 | Sawhney | |
| 6,287,588 B1 | 9/2001 | Shih et al. | |
| 6,331,311 B1 | 12/2001 | Brodbeck et al. | |
| 6,428,804 B1 | 8/2002 | Suzuki et al. | |
| 6,461,631 B1 | 10/2002 | Dunn et al. | |
| 6,589,549 B2 | 7/2003 | Shih et al. | |
| 6,630,155 B1 | 10/2003 | Chandrashekar et al. | |
| 6,632,457 B1 | 10/2003 | Sawhney | |
| 6,773,714 B2 | 8/2004 | Dunn et al. | |
| 2002/0009454 A1 | 1/2002 | Boone et al. | |
| 2002/0090398 A1 | 7/2002 | Dunn et al. | |
| 2003/0039689 A1* | 2/2003 | Chen et al. | 424/468 |
| 2004/0072799 A1 | 4/2004 | Li et al. | |
| 2004/0082540 A1 | 4/2004 | Hermida Ochoa | |
| 2004/0110734 A1* | 6/2004 | Sackeyflo et al. | 514/171 |
| 2004/0214793 A1 | 10/2004 | Hermida Ochoa | |
| 2004/0225077 A1* | 11/2004 | Gravett et al. | 525/418 |
| 2005/0142163 A1 | 6/2005 | Hunter et al. | |
| 2005/0186261 A1 | 8/2005 | Avelar et al. | |
| 2005/0197293 A1 | 9/2005 | Mellis et al. | |
| 2006/0148903 A1 | 7/2006 | Burch et al. | |
| 2006/0189944 A1 | 8/2006 | Campbell et al. | |
| 2007/0031472 A1* | 2/2007 | Huang et al. | 424/427 |
| 2007/0156180 A1 | 7/2007 | Jaax et al. | |
| 2007/0202074 A1 | 8/2007 | Shalaby | |
| 2007/0243225 A1 | 10/2007 | McKay | |
| 2007/0243228 A1 | 10/2007 | McKay | |
| 2008/0038316 A1* | 2/2008 | Wong et al. | 424/426 |
| 2008/0091207 A1 | 4/2008 | Truckai et al. | |
| 2008/0317805 A1* | 12/2008 | McKay et al. | 424/422 |

FOREIGN PATENT DOCUMENTS

WO 03005961 A2 1/2003

OTHER PUBLICATIONS

Raisz, Pathogenesis of Osteoporosis: Concepts, Conflicts, and Prospects, J. Clin. Invest., vol. 115, Issue 12, pp. 3318-3325 (2005).*
Brooks, Inflammation as an Important Feature of Osteoarthritis, Bull. of the World Health Org., vol. 81, Issue 9, pp. 689-690 (2003).*
Muldrew, Osteoarthritis as an Inevitable Consequence of the Structure of Articular Cartilage, Medical Hypotheses, vol. 59, Issue 4, pp. 389-397 (2002).*
Ranganathan, Genetics of Bone Loss in Rheumatoid Arthritis—Role of Vitamin D Receptor Polymorphisms, Rheumatology (Oxford), vol. 48, Issue 4, pp. 342-346 (2009).*
QLT Inc., Atrigel Sheet, 2 pages, Drug Delivery Platform, Revised Jul. 2006.
Hall, Topical Fluocinolone in Rheumatoid Arthritis, Ann.rheum. Dis. (1967), 26, pp. 260-261.
Seyfried, Perspectives in Biology and Medicine. 2009 Project MUSE© , vol. 44, No. 2, Spring 2001, 1 page "Abstract Only".
Martinez, Macrophage Activation and Polarization, 2008, 1 page "Abstract Only".
Kockx, Apoptosis in atherosclerosis: beneficial or detrimental?, Cardiovascular Research, Oxford Journals, vol. 45, No. 3, (2000), 20 pages.

* cited by examiner

*Primary Examiner* — Frederick Krass
*Assistant Examiner* — Dennis J Parad
(74) *Attorney, Agent, or Firm* — Sorell Lenna & Schmidt LLP

(57) ABSTRACT

Effective treatments for protecting against undesirable macrophage activity are provided. Through the administration of an effective amount of fluocinolone at or near a target site, one can reduce or prevent macrophage activity. In various embodiments, fluocinolone formulations may be provided within biodegradable polymers to prevent transplant rejection for at least thirty days. In some embodiments, the relief can be for at least sixty days, or up to ninety days.

13 Claims, 12 Drawing Sheets

FLUOCINOLONE IMPLANTS TO PROTECT AGAINST UNDESIRABLE BONE AND CARTILAGE DESTRUCTION

This application claims the benefit of the filing date of U.S. Provisional Patent Application No. 61/046,218 filed Apr. 18, 2008 and entitled "Fluocinolone Formulations In A Biodegradable Polymer Carrier." U.S. Provisional Patent Application No. 61/046,218 is hereby incorporated by reference into the present disclosure.

BACKGROUND

Macrophage cells provide the human body with the ability to clear out or to remove dead or decaying cells. Their primary mechanism for accomplishing this task is to engulf and then to digest cellular debris and pathogens, and they can act as either stationary or mobile cells, and stimulate lymphocytes and other immune cells to respond to pathogens. In many circumstances this is a highly desirable action.

However, macrophages can also target materials in the body that the host organism would prefer were left in place. For example, macrophage cells have been indicated as the major mechanism through which inflammatory cytokines are produced in rheumatic arthritis and in turn can lead to the deleterious removal of cartilage. Macrophages have also been implicated in the immunologically distinct condition of osteoarthritis.

To date interventions for conditions such as rheumatoid arthritis and osteoarthritis have focused on treating the resulting inflammation and pain but not the upstream causes of these symptoms. Thus, although this may provide some relief from the symptoms of inflammation and pain; however, the underlying condition remains a problem. Accordingly, there is a need to provide effective treatments to prevent undesirable macrophage recruitment, which in turn may prevent the production of substances that cause the problems such as the inflammatory cytokines.

SUMMARY

Fluocinolone is a corticosteroid that in known to have anti-inflammatory properties. However, the present inventors have appreciated that it may also be used to reduce or to prevent undesirable macrophage activity upstream of the inflammatory response by minimizing macrophage recruitment in the first place, which is implicated in diseases such as arthritis. Accordingly, the present application provides compositions comprising fluocinolone or its pharmaceutically acceptable salts that are administered in order to reduce or to prevent destruction of bone and/or cartilage and thus has an osteoprotective effect or protects the cartilage as it reduces undesirable macrophage present and subsequent activity. The present application also provides methods of treatment that use these materials. In various embodiments, the fluocinolone or its pharmaceutically acceptable salt may be administered to reduce or to prevent arthritic conditions. In some embodiments, these compositions and methods may be designed for long duration release of fluocinolone that has been internally placed.

According to one embodiment, there is a pharmaceutical formulation comprising: fluocinolone, wherein the fluocinolone or a pharmaceutically acceptable salt thereof comprises from about 300 micrograms to about 350 micrograms of the formulation, and at least one biodegradable polymer. The pharmaceutical composition may for example, be part of a drug depot. The drug depot may: (i) consist of only the fluocinolone (or one or more of its pharmaceutically acceptable salts) and the biodegradable polymer(s); or (ii) consist essentially of the fluocinolone (or one or more of its pharmaceutically acceptable salts) and the biodegradable polymer(s); or (iii) comprise the fluocinolone (or one or more of its pharmaceutically acceptable salts), the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the formulation.

According to another embodiment, there is a pharmaceutical formulation comprising fluocinolone or a pharmaceutically acceptable salt thereof, wherein the fluocinolone or a pharmaceutically acceptable salt thereof comprises from about 0.5 wt. % to about 20 wt. % of the formulation, and at least one biodegradable polymer, wherein the at least one biodegradable polymer comprises poly(lactic-co-glycolic acid) or poly(orthoester) or a combination thereof, and the at least one biodegradable polymer comprises at least 80 wt. % of the formulation.

According to another embodiment, there is an implantable drug depot for reducing or preventing bone and/or cartilage destruction in a patient in need of such treatment, the implantable drug depot comprising fluocinolone or a pharmaceutically acceptable salt thereof in an amount from about 0.05 wt. % to about 25 wt. % of the formulation, and at least one biodegradable polymer.

According to another embodiment, there is an implantable drug depot for reducing or preventing bone and/or cartilage destruction in a patient in need of such treatment, the implantable drug depot comprising fluocinolone or a pharmaceutically acceptable salt thereof in an amount of from about 0.5 wt. % to about 20 wt. % of the drug depot, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

According to another embodiment, there is an implantable drug depot for reducing or preventing bone and/or cartilage destruction in a patient in need of such treatment, the implantable drug depot comprising fluocinolone or a pharmaceutically acceptable salt thereof in an amount of from about 0.5 wt. % to about 25 wt. % of the drug depot, and at least one polymer, wherein the at least one polymer comprises one or more of poly(lactide-co-glycolide), D-lactide, D,L-lactide, L-lactide, D,L-lactide-caprolactone, and D,L-lactide-glycolide-caprolactone.

According to another embodiment, there is a method of making an implantable drug depot, the method comprising combining a biocompatible polymer and a therapeutically effective amount of the fluocinolone or a pharmaceutically acceptable salt thereof and forming the implantable drug depot from the combination.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims.

DETAILED DESCRIPTION

Figure 1:
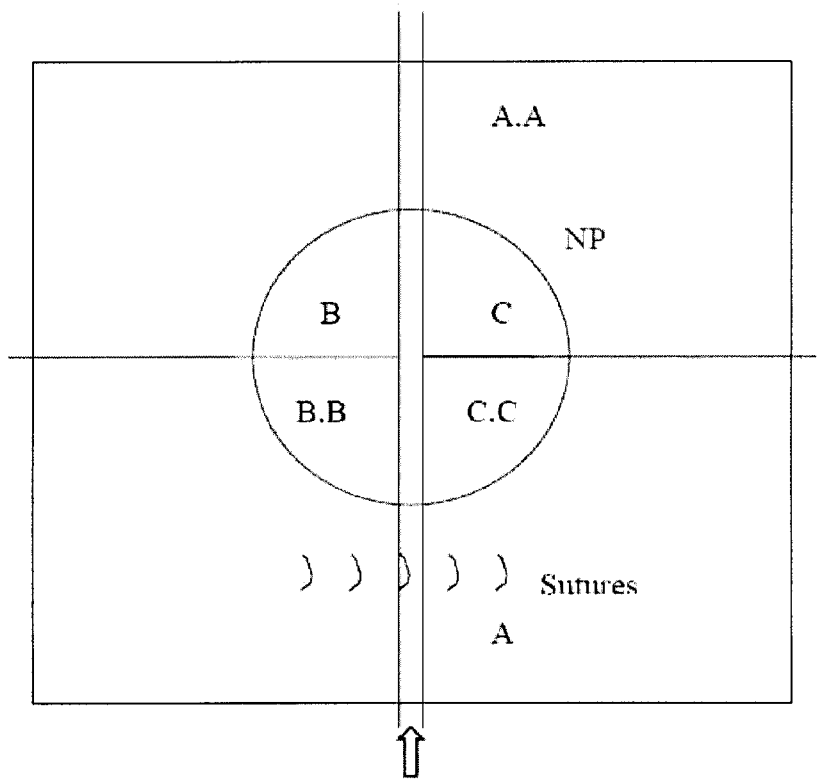
FIG. 1 is representation of the NP (nucleus pulposus taken from the inter-vertebral disc from the spinal cord) of the layout of the slides that appear in FIGS. 2-12.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the fluocinolone is administered to the body. Thus, a drug depot may comprise a physical structure to facilitate implantation and retention in a desired site. The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 10 cm from the administration site and comprises fluocinolone. A drug depot may also include a pump or pellet. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

A "therapeutically effective amount" or "effective amount" is such that when administered, the drug results in alteration of the biological activity, such as, for example, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrase "undesirable macrophage activity" refers to the activity of macrophages that are destructive to an organism including the self-destructive activity of breaking down cartilage or bone. The prevention or reduction of this undesirable macrophage activity may thus have either an osteoprotective or cartilage protective function. For example, through the methods and formulations, some embodiments may prevent at least 10%, at least 20%, as least 30%, at least 40%, at least 50%, at least 60%, at least 70%, at least 80%, at least 90% or at least 100% of the break down of bone and/or cartilage that might otherwise occur in a patient in need of such treatment.

The two types of formulations (sustain release and immediate release) may be used in conjunction. For example, one can use a mixture of formulations that provide different release profiles, either by use of different forms of the drug or by mixtures of different formulations of sustained release materials. The sustained release and immediate release may be in one or more of the same depots. In various embodiments, the sustained release and immediate release may be part of separate depots. For example a bolus or immediate release formulation of fluocinolone may be placed at or near the target site and a sustain release formulation may also be placed at or near the same site or be provided within the same formulation through a combination of different polymer matrices and/or drug forms. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four hours after implantation. "Initial burst" or "burst effect" or "bolus dose" refers to the release of therapeutic agent from the depot during the first twenty-four hours after the depot comes in contact with an aqueous fluid (e.g., synovial fluid, cerebral spinal fluid, etc.). The "burst effect" is believed to be due to the increased release of therapeutic agent from the depot. In alternative embodiments, the depot (e.g., gel) is designed to avoid this initial burst effect.

"Treating" or "treatment" of a disease or condition refers to executing a protocol that may include administering one or more drugs to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. Some conditions of pain and/or inflammation include chronic conditions, such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, tissue or organ transplant rejection or the like. "Reducing inflammation" includes a decrease in inflammation and/or rejection and does not require complete alleviation of signs or symptoms of inflammation or rejection, and does not require a cure. In various embodiments, reducing inflammation includes even a marginal decrease in inflammation and/or issue or organ rejection.

The term "pain" includes nociception and the sensation of pain, both of which can be assessed objectively and subjectively, using pain scores and other methods well-known in the art. In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well-known in the art. Exemplary types of pain reducible, preventable or treatable by the methods and compositions disclosed herein include, without limitation, lower back pain, neck pain, leg pain, radicular pain, or abdominal pain from abdominal surgery, and neuropathic pain of the arm, neck, back, lower back, leg, and related pain distributions resulting from disk or spine surgery.

"Localized" delivery includes delivery where one or more drugs are deposited within a tissue, for example, at a nerve root of the nervous system or a region of the brain, or in close proximity (within about 10 cm, or preferably within about 5 cm or preferably within about 0.1 cm, for example) thereto.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "release rate profile" refers to the percentage of active ingredient that is released over fixed units of time, e.g., mcg/hr, mcg/day, 10% per day for ten days, etc. As persons of ordinary skill know a release rate profile may, but need not, be linear.

The term "solid" is intended to mean a rigid material, while "semi-solid" is intended to mean a material that has some degree of flexibility, thereby allowing the depot to bend and conform to the surrounding tissue requirements.

"Targeted delivery system" provides delivery of one or more drugs depots, gels or depots dispersed in the gel having a quantity of therapeutic agent that can be deposited at or near the target site as needed.

The phrase "target site" refers to the site at which symptoms and/or causes of a disorder occur, for example, it may be a site at which macrophages causes the destruction of cartilage at a joint.

The term "tissue" refers to any body tissue or organ from or within an organism, including but not limited to pancreatic tissue, liver tissue, skin tissue, kidney tissue, heart tissue, etc.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide).

The abbreviation "PLA" refers to polyglycolide.

The abbreviation "POE" refers to poly(orthoester)

The term "arthritis" refers to a group of conditions involving damage to the joints of the body. There are different forms of arthritis; each has a different cause. The most common form of arthritis is osteoarthritis, which is also known as degenerative joint disease, and is a result of trauma to the joint, infection of the joint, or age. Other arthritis forms include but are not limited to rheumatoid arthritis, psoriatic arthritis, autoimmune diseases in which the body attacks itself, and gouty arthritis, which is caused by deposition of uric acid crystals in the joint.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Fluocinolone

When referring to fluocinolone, unless otherwise specified or apparent from context it is understood that the inventors are also referring to pharmaceutically acceptable salts. One common form of fluocinolone for administration to mammals is fluocinolone acetonide. Examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to fluocinolone the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA.

The fluocinolone or its pharmaceutically acceptable salt may be administered with a muscle relaxant. Exemplary muscle relaxants include by way of example and not limitation, alcuronium chloride, atracurium bescylate, baclofen, carbamate, carbolonium, carisoprodol, chlorphenesin, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may comprise other therapeutic agents in addition to the fluocinolone as well. These therapeutic agents, in various embodiments, block the transcription or translation of TNF-α or other proteins in the inflammation cascade. Suitable therapeutic agents include, but are not limited to, integrin antagonists, alpha-4beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin. or tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, alfentanil, amitriptyline, bupivicaine, lidocaine, opioid analgesics such as buprenorphine, butorphanol, carbamazepine, codeine, dextromoramide, dextropropoxyphene, dezocine, dextropropoxyphene, diamorphine, dihydrocodeine, eptazocine, fentanyl, flupirtine, gabapentin hydrocodone, hydromorphone, ketobemidone, levomethadyl, mepiridine, methadone, meptazinol, morphine, nalbuphine, opium, oxycodone, papaveretum, pentazocine, pethidine, phenoperidine, piritramide, pregabalin, remifentanil, sufentanil, tilidine, tramadol, or a combination thereof.

The fluocinolone may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s). Non-biodegradable polymers include but are not limited to PVC and polyurethane.

In some embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodable, a bioabsorbable, and/or a biodegradable biopolymer that may provide immediate release, or sustained release of the fluocinolone. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

Exemplary excipients include but are not limited to mPEG, D-Sorbital, maltodextran, cyclodextrin and combinations thereof. The excipients, when present may for example be present in an amount of from about 0.05 wt. % to about 85 wt. %.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the depot.

Gel

In various embodiments, the fluocinolone is administered in a gel. The gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1\times10^4$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, a depot comprises an adherent gel comprising fluocinolone that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1\times10^4$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times10^4$ to about $2\times10^6$ dynes/cm$^2$, or $1\times10^5$ to about $7\times10^5$ dynes/cm$^2$, or $2\times10^5$ to about $5\times10^5$ dynes/cm$^2$. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, and about 0.80 to about 1.00 dL/g.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The molecular weight of the polymer can be varied to regulate the release rate profile and/or delivery duration of the active ingredient. In general, as the molecular weight of the polymer increases, one or more of the following occurs: the burst index is lower, the release profile is flatter and/or the duration of delivery is longer. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time. By was of a non-limiting example, the polymer make up may comprise from 50:50 PLGA to 100 PLA and the molecular weight range may be from 0.45 to 0.8 dI/g.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition, which includes a low-molecular weight polymer. Polymeric gel formulations that include high molecular weight polymers, also tend to have a higher solution viscosity than a polymeric gel, which include a low-molecular weight polymer.

As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G/CL or G/CL ration for a given polymer) there will be a resulting depot composition having a regulated burst index and duration of delivery. For example, a depot composition having a polymer with a L/G ration of 50:50 has a short duration of delivery ranging from about two days to about one month; a depot composition having a polymer with a L/G ratio of 65:35 has a duration of delivery of about two months; a depot composition having a polymer with a L/G ratio of 75:25 or L/CL ratio of 75:25 has a duration of delivery of about three months to about four months; a depot composition having a polymer ratio with a L/G ratio of 85:15 has a duration of delivery of about five months; a depot composition having a polymer with a L/CL ratio of 25:75 or PLA has a duration of delivery greater than or equal to six months; a depot composition having a terpolymer of CL/G/L with G greater than 50% and L greater than 10% has a duration of delivery of about one month and a depot composition having a terpolymer of CL/G/L with G less than 50% and L less than 10% has a duration months up to six months. In general, increasing the G content relative to the CL content shortens the duration of delivery whereas increasing the CL content relative to the G content lengthens the duration of delivery.

Thus, depot compositions having a blend of polymers having different molecular weights, end groups and comonomer ratios can be used to create a depot formulation having a lower burst index and a regulated duration of delivery.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the gel, microspheres may be dispersed within the gel, the microspheres being loaded with fluocinolone. In one embodiment, the microspheres provide for a sustained release of the fluocinolone. In yet another embodiment, the gel, which is biodegradable, prevents the microspheres from releasing the fluocinolone; the microspheres thus do not release the fluocinolone until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the fluocinolone.

Microspheres, much like a fluid, may disperse relatively quickly, depending upon the surrounding tissue type, and hence disperse the fluocinolone. In some situations, this may be desirable; in others, it may be more desirable to keep the fluocinolone tightly constrained to a well-defined target site. The present invention also contemplates the use of adherent gels to so constrain dispersal of the therapeutic agent. These gels may be deployed, for example, in a disc space, in a spinal canal, or in surrounding tissue.

Drug Delivery

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, X-ray, or other imaging techniques. In such embodiments, the transparent or translucent portion may include a radiopaque material or ultrasound responsive topography that increases the contrast of the needle or cannula relative to the absence of the material or topography.

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms. They leave no residues and do not have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

In various embodiments, a kit is provided that may include additional parts along with the drug depot and/or medical device combined together to be used to implant the drug depot. The kit may include the drug depot device in a first compartment. The second compartment may include a canister holding the drug depot and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. A fifth compartment may comprise an agent for radiographic imaging. Each tool may be separately packaged in a plastic pouch that is radiation sterilized. A cover of the kit may include illustrations of the implanting procedure and a clear plastic cover may be placed over the compartments to maintain sterility.

In various embodiments, a method for delivering a therapeutic agent into a site of a patient is provided, the method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, to administer the gel having the drug depot dispersed therein to the desired site, first the cannula or needle can be inserted through the skin and soft tissue down to the target tissue site and the gel administered at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Although the spinal site is described above, the drug depot can be delivered to any site beneath the skin, including, but not limited to, at least one muscle, ligament, tendon, cartilage, spinal disc, spinal foraminal space, near the spinal nerve root, or spinal canal. The drug depot may also be administered locally to any site at which there is undesirable macrophage activity, including but not limited to arthritic site such as the joints of the hand, finger, wrist, elbow, shoulder, knee, ankle hip, foot, toe, pelvis and neck.

The fluocinolone-based formulation of the present application may be used as medicaments in the form of pharmaceutical preparations. The preparations may be formed in an administration with a suitable pharmaceutical carrier that may be solid or liquid and organic or inorganic, and placed in the appropriate form for parenteral or other administration as desired. As persons of ordinary skill are aware, known carriers include but are not limited to water, gelatine, lactose, starches, stearic acid, magnesium stearate, sicaryl alcohol, talc, vegetable oils, benzyl alcohols, gums, waxes, propylene glycol, polyalkylene glycols and other known carriers for medicaments.

Parenteral administration may additionally include, for example, an infusion pump that administers a pharmaceutical composition through a catheter, an implantable mini-pump that can be inserted at or near the target site, an implantable controlled release device or sustained release delivery system that can release a certain amount of the composition per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Another embodiment of the present invention is directed to a method for treating a mammal that has received a tissue transplant, said method comprising administering a therapeutically effective amount of fluocinolone at a target site beneath the skin. The fluocinolone (or pharmaceutically acceptable salt) may for example be administered locally to the target tissue site as a drug depot.

In some embodiments, the fluocinolone is encapsulated in a plurality of depots comprising microparticles, microspheres, microcapsules, and/or microfibers.

In some embodiments there is a method for making an implantable drug depot. The method may comprise combining a biocompatible polymer and a therapeutically effective amount of fluocinolone or a pharmaceutically acceptable salt thereof and forming the implantable drug depot from the combination.

In some embodiments, the fluocinolone is suitable for parenteral administration. The term "parenteral" as used herein refers to modes of administration that bypass the gastrointestinal tract, and include for example, intravenous, intramuscular, continuous or intermittent infusion, intraperitoneal, intrasternal, subcutaneous, intra-operatively, intrathecally, intradiskally, peridiskally, epidurally, perispinally, intraarticular injection or combinations thereof. In some embodiments, the injection is intrathecal, which refers to an injection into the spinal canal (intrathecal space surrounding the spinal cord). An injection may also be into a muscle or other tissue.

In various embodiments, the drug depot comprising the fluocinolone can be made by combining a biocompatible polymer and a therapeutically effective amount of fluocinolone or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: fluocinolone and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: fluocinolone, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, fluocinolone may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the fluocinolone containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., fluocinolone), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of fluocinolone because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such as fluocinolone is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, fluocinolone is used and mixed or sprayed with the PLGA or PEG550 polymer, and the resulting depot may be formed by extrusion and dried.

In various embodiments, there is a pharmaceutical formulation comprising: fluocinolone, wherein the fluocinolone comprises from about 0.05 wt. % to about 25 wt. % of the formulation, and at least one biodegradable polymer. In some embodiments, the pharmaceutical the fluocinolone comprises from about 3 wt. % to about 20 wt. %, about 3 wt. % to about 18 wt. %, about 5 wt. % to about 15 wt. % or about 7.5 wt. % to about 12.5 wt. % of the formulation.

In some embodiments, the at least one biodegradable polymer comprises poly(lactic-co-glycolic acid) (PLA) or poly (orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In some embodiments, the biodegradable polymer comprises at least 50 wt. % of the formulation, at least about 60 wt. % of the formulation, at least about 70 wt. % of the formulation, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the fluocinolone are the only components of the pharmaceutical formulation.

In some embodiments, at least 75% of the particles have a size from about 1 micrometer to about 30 micrometers. In some embodiments, at least 85% of the particles have a size from about 1 micrometer to about 30 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

In some embodiments, there is a pharmaceutical formulation comprising: fluocinolone, wherein said fluocinolone comprises from about 0.05 wt. % to about 25 wt. % of the formulation, and at least one biodegradable polymer, wherein the at least one biodegradable polymer comprises poly(lactic-co-glycolic acid) or poly(orthoester) or a combination thereof, and said at least one biodegradable polymer comprises at least 80 wt. % of said formulation.

In some embodiments, there are methods for treating arthritic conditions, including but not limited to rheumatoid arthritis, psoriatic arthritis, osteoarthritis and pathogen-induced arthritic conditions, for example, Lyme disease arthritis, bacterially induced arthritis, and polioarthritis. These methods comprise: administering a pharmaceutical composition to an organism, wherein said pharmaceutical composition comprises from about 0.05 wt. % to about 25 wt. % of the formulation, and at least one biodegradable polymer. In some embodiments, the loading is from about 5 wt. % to about 10 wt. %. In some embodiments, the loading is from about 10 wt. % to about 20 wt. %.

In some embodiment there is a higher loading of fluocinolone, e.g., at least 20 wt. %, at least 30 wt. %, at least 40 wt. %, at least 50 wt. %, at least 60 wt. %, at least 70 wt. %, at least 80 wt. %, or at least 90 wt. %.

A strategy of triangulation may be effective when administering these pharmaceutical formulations. Thus, a plurality (at least two, at least three, at least four, at least five, at least six, at least seven, etc.) drug depots comprising the pharmaceutical formulations may be placed around the target tissue site such that the target tissue site falls within a region that is either between the formulations when there are two, or within an area whose perimeter is defined by a set of plurality of formulations.

In some embodiments, the formulations are slightly rigid with varying length, widths, diameters, etc. For example, certain formulations may have a diameter of 0.75 mm and a length of 3 mm. It should be noted that particle size may be altered by techniques such as mortar and pestel, jet-drying or jet milling.

Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and 0.002 to approximately 0.025 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day. Dosing formulations may be prepared to contain a sufficient amount of the active ingredient to enable the desired about of compound to be release over the desired amount of time.

In some embodiments, there is sufficient fluocinolone such that the fluocinolone is released at a rate of 2-3 µg per day for a period of at least three days. In some embodiments, this release rate continues for, at least ten days, at least fifteen days, at least twenty-five days, at least thirty days, at least fifty days, at least ninety days, at least one hundred days, at least one-hundred and thirty-five days, at least one-hundred and fifty days, or at least one hundred and eighty days.

For some embodiments, 300-350 micrograms of fluocinolone as formulated with a biopolymer are implanted into a person at or near a target tissue site. In some embodiments, the 300 micrograms to about 325 micrograms of fluocinolone as formulated with a biopolymer are implanted into a person at or near a target tissue site. In some embodiments, the 325 micrograms to about 350 micrograms of fluocinolone as formulated with a biopolymer are implanted into a person at or near a target tissue site. If fluocinolone is implanted at multiple sites that triangulate the target site then in some embodiments, the total amount of fluocinolone at each site is a fraction of the total 300-350 micrograms. For example, one may implant a single does of 324 micrograms at one site, or two separate doses of 162 micrograms at two sites, or three separate dose of 108 micrograms at three sites that triangulate the tissue site. It is important to limit the total dosage to an amount less than that which would be harmful to the organism. However, in some embodiments, although when there are a plurality of sites each site may contain less than the total does that might have been administered in a single application, it is important to remember that each site will independent have a release profile, and the biopolymers' concentration and substance should be adjusted accordingly to ensure that the sustain release occurs over sufficient time.

In some embodiments, there is a drug depot comprising fluocinolone or fluocinolone and a polymer, wherein the polymer is one more of poly(lactide-co-glycolide) (PLGA), D-lactide, D,L-lactide, L-lactide, D,L-lactide-caprolactone, and D,L-lactide-glycolide-caprolactone.

The present invention may be used to target any undesirable macrophage activity, including but not limited to the site the rheumatoid arthritis or osteoarthritis.

When developing formulations it in important to balance the limited space in which the activity can take place, with the goal of an extended release period that may for example, be between 30 and 90 days, between 30 and 40 days, between 40 and 50 days, between 50 and 60 days, between 60 and 70 days, between 70 and 80 days or between 80 and 90 days. A sufficient amount of fluocinolone should be present in order to release therapeutic amounts over the desired time period.

Exemplary pellets may comprise fluocinolone and PLGA and be 0.5 to 1.5 mm long and 0.5 to 1.0 mm in diameter. In some embodiments, at least one or exactly one, at least two or exactly two, at least three or exactly three pellets are placed less than about 2.0 cm, less than about 1.5 cm, less than about 1.0 cm or less than about 0.5 cm from the site of interest.

Additionally, in some embodiments it may be desirable to combine the fluocinolone with additional anti-inflammatory compounds, analgesics, anti-microbial compounds or combinations thereof.

When administering the drug depots, it may be advantageous for the drug depots to be in the form of pellets that are injected in a formulation that can adhere to the desired location, for example the joints of the hand, foot, fingers, toes, knees, elbows or shoulders.

Having now generally described the invention, the same may be more readily understood through the following reference to the following example, which is provided by way of illustration and are not intended to limit the present invention unless specified.

EXAMPLES

Example 1

Summary

Fluocinolone-eluting pellets were evaluated for their ability to modify the resorption and inflammatory response to subcutaneously implanted inter-vertebral disc material [nucleus pulposus (NP)] in three groups of five young female Sprague-Dawley rats three days after NP implantation. The greatest resorption and least inflammatory response was observed in Group 1 (fluocinolone pellet in same pocket as NP) based on both residual NP weight (n=4) and histological evaluation (n=1). Although not as pronounced as Group 1, treatment Group 2 in which the fluocinolone pellet was placed 1.5 cm from the NP implant also has increased resorption as compared to Group 3, the control pellet treatment group.

Objective:

The objective of the study was to evaluate the effect of fluocinolone-releasing pellets or control pellets on the resorption rate of subcutaneously implanted donor nucleus pulposus (NP) inter-vertebral disc material.

Materials and Methods:

The NP was removed from a total of eight discs from each of fifteen donor female Sprague-Dawley rats. The collected NP from each rat was pooled, weighed, and placed in a subcutaneous abdominal pocket of a single recipient female, Sprague-Dawley rat. The fifteen recipient rats were randomly assigned to treatment groups of five animals each as described in the table below. Group 1 received a fluocinolone-eluting pellet in the same subcutaneous pocket as the NP material and had a surgical empty shame pocket created 1.5 cm away. Group 2 received NP material in a subcutaneous pocket and had a fluocinolone-eluting pellet placed in a subcutaneous pocket 1.5 cm away. Group 3 received NP material in a subcutaneous pocket and had a control pellet with no test article placed in a subcutaneous pocket 1.5 cm away.

| TG | Implant | Location of Implant | N |
|---|---|---|---|
| 1 | Fluocinolone-eluting PLGA pellet | Same pocket as NP (FLU-0 cm) + empty sham pocket 1.5 cm away | 5 + 5* |
| 2 | Fluocinolone-eluting PLGA pellet | Separate pocket from NP, 1.5 cm away (FLU-1.5 cm) | 5 + 5* |
| 3 | Control pellet | Separate pocket from NP, 1.5 cm away (FLU-1.5 cm) | 5 + 5* |

*Second groups were donor animals that were used for NP collection.

Three days post surgery, animals were anesthetized, blood was collected for fluocinolone levels and the animals were euthanized. The residual NP from 4 of the 5 animals per treatment group was collected and weighed. Tissue was collected from the remaining animal in each treatment group, fixed in 10% neutral buffered formalin, processed, embedded in paraffin, sectioned and stained with hematoxylin ad eosin for histological evaluation. A single slide was prepared through the center of the second, distant subcutaneous pocket containing surgical lesions (Sham control-Group 1), the fluocinolone-eluting pellet (Group 2), or the control pellet (Group 3) but no NP. Slides were evaluated for the inflammatory response and the extent of residual NP. For NP containing tissue, slides were labeled: A, AA, B, BB, C or CC as depicted in FIG. 1. For the distant subcutaneous pocket, a single cross-section was obtained and the slide was labeled D.

Figure 2:
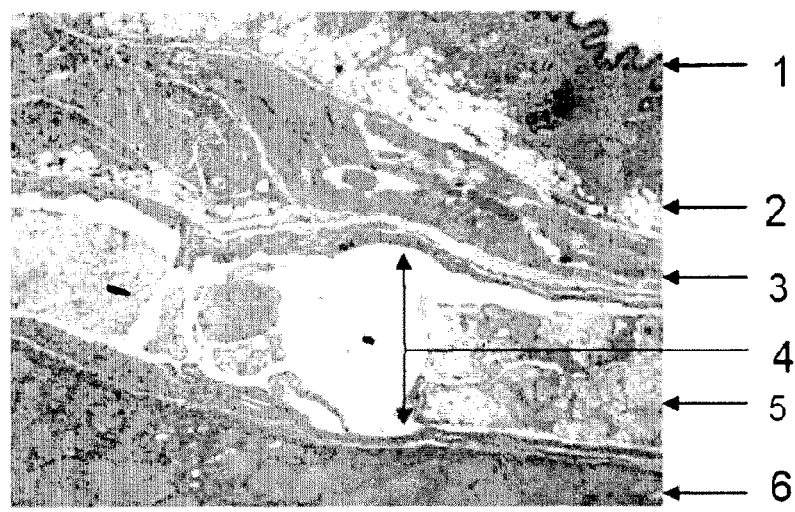
FIG. 2 is a representation of a slide taken from Animal 267 at 4× objective.
Figure 3:
FIG. 3 is a representation of a slide taken from Animal 267 at 10× objective.
Figure 4:
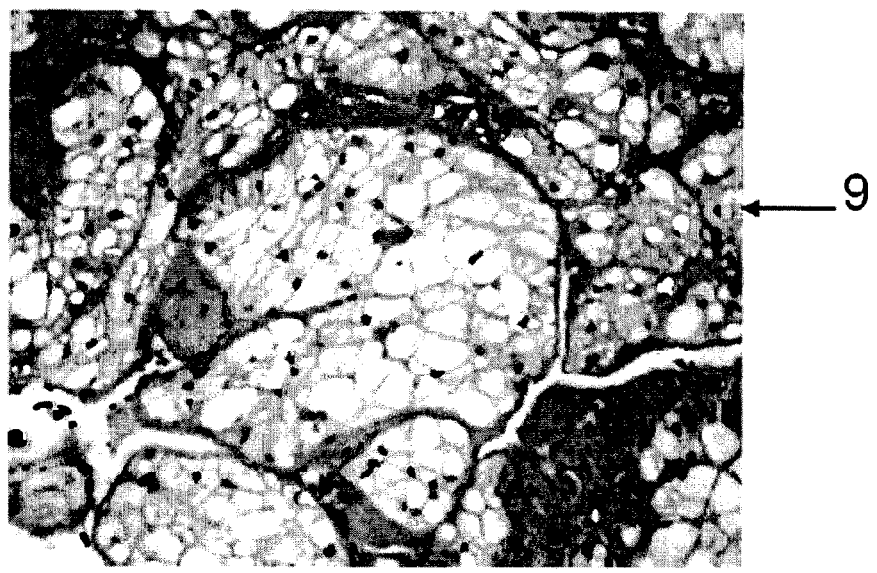
FIG. 4 is a representation of a slide taken from Animal 267 at 20× objective.

Group 1:

Animal 267 (sections A, AA, B, BB, C, and CC): A cross section and lateral margins through the site of NP implantation were evaluated. Residual NP was visible in sections A, AA, B and BB. Residual inflammation, but not NP was observed in sections C and CC. The residual NP had lost the majority of its basophilic amorphous appearance and was largely replaced by large eosinophilic foamy macrophages. Foamy macrophages containing residual NP were surrounded by a fairly thin, pseudo epithelial layer consisting of well organized loose connective tissue, and smaller numbers of monocytes, macrophages and occasional neutrophils. Inflammatory cells occasionally extended into the subjacent dermis and muscularis. Representative examples of the changes are depicted in FIGS. 2-4. FIG. 2 shows a slide of animal 267 at 4× objective with reference being made to the skin surface 1, subcutaneous fat 2, subcutaneous muscle 3, inflammatory response 4, residual NP 5 and deep muscle layer 6. FIG. 3 shows a slide of animal 267 at 10× objective with reference being made to inflammatory response 7 and residual NP 8. FIG. 4 shows a slide of animal 267 at 20× objective with reference being made to residual NP 9. Note that reference 9 shows a foamy appearance and cellular dots that are interpreted as foamy macrophages involved in phagocytosis.

Figure 5:
FIG. 5 is a representation of a slide taken from Animal 266 at 4× objective.
Figure 6:
FIG. 6 is a representation of a slide taken from Animal 266 at 10× objective.
Figure 7:
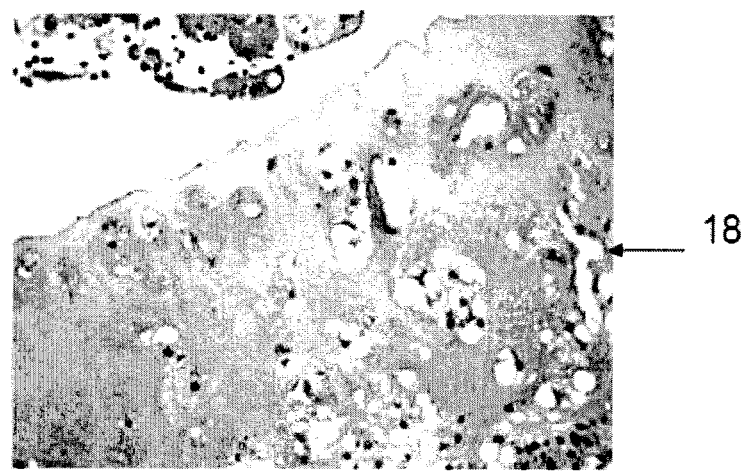
FIG. 7 is a representation of a slide taken from Animal 266 at 20× objective.

Group 2:

Animal 266 (sections A, AA, B, BB, C, and CC): A cross section and lateral margins through the site of NP implantation were evaluated. Residual NP was detected only in section C. Sections A, AA, and CC contained pseudo epithelial pockets and inflammation, but the center of the pocket was empty. Sections B and BB appear to be outside of the original site, in that they did not contain NP or residual inflammatory infiltrates and consisted of normal tissue. The residual NP was predominantly acellular and retained its basophilic staining qualities with a small to moderate number of foamy macrophages embedded within the residual NP matrix. The residual NP was most commonly surrounded by a densely cellular, relatively thick, pseudo epithelial layer consisting of fairly well organized loose connective tissue, monocytes, macrophages and small of neutrophils. Inflammatory cells occasionally extended into the subject dermis and muscularis. Representative examples of the changes are depicted in FIGS. 5-7. FIG. 5 shows a slide of animal 266 at 4× objective with reference being made to the muscle 10, inflammation/pseudocapsule 11, NP 12, inflammation/pseudocapsule 13, muscle 14, and subcutaneous fat 15. FIG. 6 shows a slide of animal 266 at 10× objective with reference being made to inflammation 16 and NP 17. FIG. 7 shows a slide of animal 266 at 20× objective with reference being made to residual NP 18, showing a reduced number of macrophages.

Figure 8:
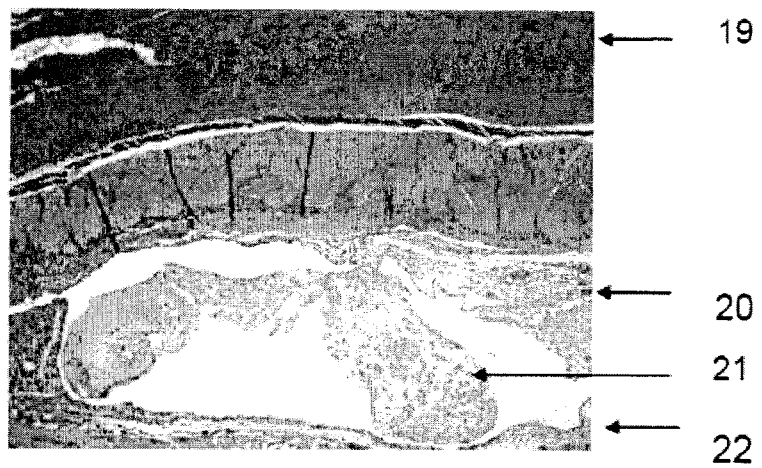
FIG. 8 is a representation of a slide taken from Animal 265 at 4× objective.
Figure 9:
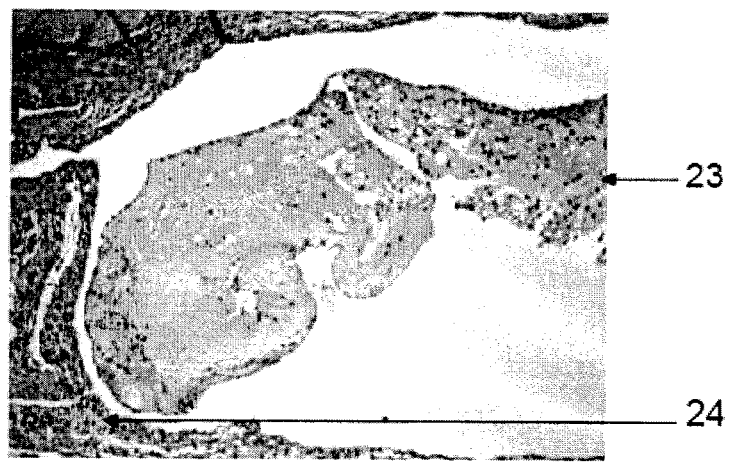
FIG. 9 is a representation of a slide taken from Animal 265 at 10× objective.
Figure 10:
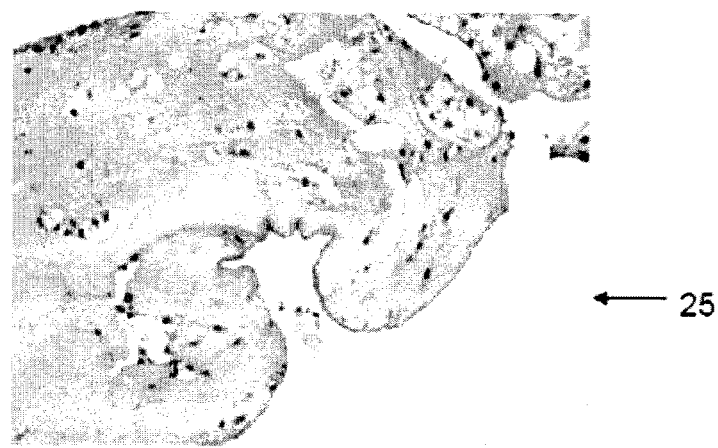
FIG. 10 is a representation of a slide taken from Animal 265 at 20× objective.

Group 3:

Animal 265 (sections A, AA, B, BB, C, and CC): A cross section and lateral margins through the site of NP implantation were evaluated. NP (characterized by an amorphous, lightly basophilic and poorly cellular material) was observed in the cross sectional slides (A and AA), but not the slides representing the lateral margins (B, BB, C or CC). Variable amounts of NP remained depending upon the section evaluated. In some areas of the slide, the residual NP was largely acellular and retained its basophilic staining qualities (approximately 50%). In other areas, the NP had a foamy, lightly eosinophilic and moderately cellular appearance that was interpreted as partial phagocytic degradation of the NP by foamy macrophages. The residual NP was most commonly surrounded by a densely cellular, relatively thick, pseudo epithelial layer consisting of fairly well organized loose connective tissue, monocytes, macrophages and a small number of neutrophils. In other areas, (not depicted in the figures), the residual NP was surrounded by very loosely arranged spindle shaped cells embedded in a lightly basophilic amorphorous matrix interpreted as loose new connective tissue. Inflammatory cells occasionally extended into the subjacent dermis muscularis. Representative examples of the changes are depicted in FIGS. 8-10. FIG. 8 shows a slide of animal 265 at 4× objective with reference being made to the muscle 19, inflammation/pseudocapsule 20, NP 21, and inflammation/pseudocapsule 22. FIG. 9 shows a slide of animal 265 at 10× objective with reference being made to NP 23 and inflammation 24. FIG. 7 shows a slide of animal 265 at 20× objective with reference being made to residual NP 25, showing a reduced number of macrophages.

Figure 11:
FIG. 11 is a representation of a slide taken from Animal 267D at 4× objective.
Figure 12:
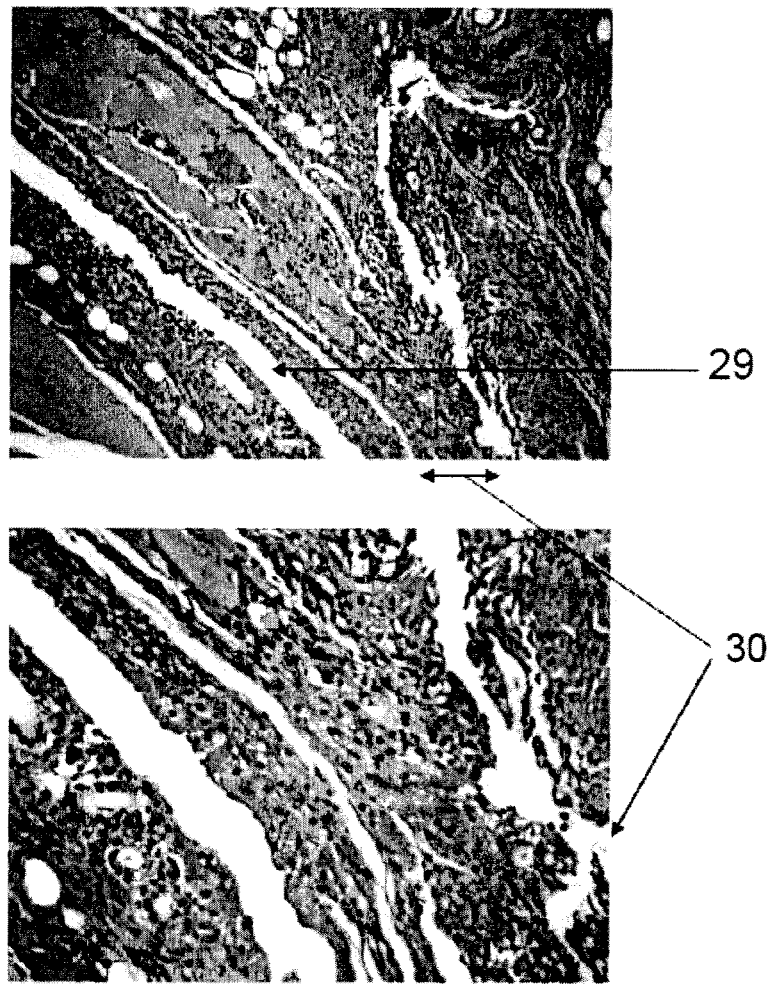
FIG. 12 is a representation of a slide taken from Animal 267D at 10× and at 20× objective.

Distant Implant Site/Sham Subcutaneous Pocket:

Two-step sections of a cross section through the "sham pocket" or distant implant site were evaluated for each animal [Animal numbers 265 (Group 3), 266 (Group 2) and 267 (Group I)]. All of the sham implant sites had a similar histological appearance and are described together. Skin sections were characterized by focally extensive subcutaneous areas of inflammatory cells, eosinophilic debris, and small amounts of collagen. In some areas, there were small, often linear, empty pockets lined by a pseudo epithelial layer of cells and small amounts of collagen. The inflammatory component was predominantly mononuclear, monocytes and lesser numbers of macrophages with occasional clusters of neutrophils. Cross sections of displaced hair shafts were occasionally noted in the area of inflammation. Inflammatory infiltrates extended, in some places, into the subjacent muscular layer and overlying dermal tissue. The changes observed in these sections are consistent with normal wound healing and are appropriate for the time period since experimental injury. Evidence of the test or control pellets implanted in animals 266 (Group 2) or 265 (Group 3) were not visible in the sections evaluated. Representative examples of the changes are depicted in FIGS. 11-12. FIG. 11 shows a slide of animal 267D at 4× objective with reference being made to the skin surface (epidermis) 26, inflammation 27 and muscle 28. FIG. 12 shows a slide of animal 267D at 10× objective and at 20× objective with reference being made to the pocket 29 and expected residual inflammation from surgery 30.

Discussion:

There were clear histological differences in the appearance of the NP implantation sites for Groups 1, 2 and 3. The Group 1 animal (#267), which had a fluocinolone-eluting pellet in the same pocket as the NP, had the most resorption of the NP material and the least inflammatory infiltrate surrounding the implanted NP. In animal 267, the NP was almost entirely replaced by large phagocytoic inflammatory macrophages and was rimmed by only a thin layer of collagen an mononuclear inflammatory cells. This histological evidence is consistent with the biological mechanism of NP resorption. The Group 2 animal (#266), which had the fluocinolone-eluting pellet in a pocket 1.5 cm from the NP material, had much more residual amorphous basophlic NP material and lesser numbers of phagocytotic foamy macrophages in the remaining NP. The inflammatory infiltrate surrounding the NP site was slightly thicker and contained more inflammatory cells than the group 1 animal. The residual NP group mean weights were higher in this group as compared to Group 1 and support the histological findings of less resoprtion as compared to Group 1. Finally, the Group 3 animal (#265), which had a control pellet in a pocket 1.5 cm from the NP pocket, had the least resorption of the NP material and the greatest inflammatory infiltrate surrounding the implant. The group mean NP weights from the group were the highest and again are consistent with the histological data.

The fluocinolone eluting pellets did modify the biologic response to NP resorption. This appears to be does dependent based on the assumption that a higher does level of fluocinolone would be locally present in Group 1 animals with the pellet implanted at the same site as compared to the Group 2 animals in which the pellet was located 1.5 cm away.

What is claimed is:

1. A method for treating arthritis, said method comprising implanting a plurality of implantable drug depots for reducing pathological bone and/or cartilage destruction caused by excessive macrophage activity in a person suffering from arthritis, each implantable drug depot comprising fluocinolone, wherein the fluocinolone is released in an amount from about 40 micrograms to about 600 micrograms per day, and each drug depot comprises at least one biodegradable polymer comprising a lactide to glycolide (L/G) ratio of 65:35 or 75:25, wherein each drug depot is a gel having a pre-dose modulus of elasticity of about $1 \times 10^4$ to about $3 \times 10^5$ dynes/cm$^2$ and a post-dose modulus of elasticity of about $1 \times 10^5$ to about $7 \times 10^5$ dynes/cm$^2$, and the plurality of drug depots are implanted to triangulate around a target site at a distance of less than about 2.0 cm from the target site, and wherein the plurality of implantable drug depots prevent at least 90% of bone and/or cartilage destruction.

2. A method according to claim 1, wherein said distance is less than about 1.5 cm from the target site.

3. A method according to claim 2, wherein said distance is less than about 1.0 cm from the target site.

4. A method according to claim 1, wherein the arthritis is rheumatoid arthritis.

5. A method according to claim 1, wherein the arthritis is osteoarthritis.

6. A method according to claim 1, wherein the target site is a joint.

7. A method according to claim 6, wherein the joint is located at an ankle, a toe, a knee, a shoulder, an elbow, a wrist, or a finger.

8. A method of treating arthritis in a mammal suffering there from, the method comprising locally administering to an affected joint, a plurality of biodegradable drug depots, each drug depot comprising fluocinolone, wherein the fluocinolone is released in an amount from about 40 micrograms to about 600 micrograms per day and reduces destruction of bone and/or cartilage of the affected joint caused by excessive macrophage activity, and wherein each drug depot is a gel comprising a polymer having a lactide to glycolide (L/G) ratio of 65:35 or 75:25 and the gel comprises a pre-dose modulus of elasticity of about $1\times10^4$ to about $3\times10^5$ dynes/cm$^2$ and a post-dose modulus of elasticity of about $1\times10^5$ to about $7\times10^5$ dynes/cm$^2$, and the plurality of biodegradable drug depots are administered so as to triangulate around the affected joint at a distance of less than about 2.0 cm from the affected joint, and wherein the plurality of implantable drug depots prevent at least 90% of bone and/or cartilage destruction.

9. A method according to claim 7, wherein the arthritis is osteoarthritis.

10. A method according to claim 8, wherein the arthritis is rheumatoid arthritis.

11. A method according to claim 8, wherein the fluocinolone is in the form of fluocinolone acetonide.

12. A method according to claim 1, wherein the L/G ratio is 65:35.

13. A method according to claim 1, wherein the L/G ratio is 75:25.

* * * * *